(12) United States Patent
Singh et al.

(10) Patent No.: US 11,504,345 B2
(45) Date of Patent: Nov. 22, 2022

(54) EXTENDED RELEASE LIQUID COMPOSITIONS OF METFORMIN

(71) Applicant: SUN PHARMACEUTICAL INDUSTRIES LIMITED, Maharashtra (IN)

(72) Inventors: Romi Barat Singh, Benares (IN); Ashish Kumar, Jhajjar (IN); Rajesh Srikrishan Shear, Gurgaon (IN); Satish Kumar Jain, Bilaspur (IN); Paras P. Jain, Amravati (IN)

(73) Assignee: SUN PHARMACEUTICAL INDUSTRIES LIMITED, Mumbai (IN)

(*) Notice: Subject to any disclaimer, the term of this patent is extended or adjusted under 35 U.S.C. 154(b) by 0 days.

(21) Appl. No.: 16/909,231

(22) Filed: Jun. 23, 2020

(65) Prior Publication Data

US 2020/0315994 A1   Oct. 8, 2020

Related U.S. Application Data

(60) Division of application No. 15/800,682, filed on Nov. 1, 2017, which is a continuation of application No. 15/144,000, filed on May 2, 2016, now abandoned, which is a continuation-in-part of application No. 15/133,773, filed on Apr. 20, 2016, now abandoned, which is a continuation of application No. PCT/IB2015/053207, filed on May 1, 2015.

(30) Foreign Application Priority Data

May 1, 2014   (IN) ........................... 1182/DEL/2014

(51) Int. Cl.
| | | |
|---|---|---|
| *A61K 31/155* | (2006.01) | |
| *A61K 9/50* | (2006.01) | |
| *A61K 9/10* | (2006.01) | |
| *A61K 9/00* | (2006.01) | |
| *A61K 47/38* | (2006.01) | |

(52) U.S. Cl.
CPC .......... *A61K 31/155* (2013.01); *A61K 9/0095* (2013.01); *A61K 9/10* (2013.01); *A61K 9/5042* (2013.01); *A61K 9/5047* (2013.01); *A61K 47/38* (2013.01)

(58) Field of Classification Search
CPC .. A61K 31/155; A61K 9/5047; A61K 9/5042; A61K 9/10; A61K 9/0095; A61K 47/38
See application file for complete search history.

(56) References Cited

U.S. PATENT DOCUMENTS

| | | |
|---|---|---|
| 3,156,369 A | 11/1964 | Bowes et al. |
| 3,603,469 A | 9/1971 | Magni |
| 3,632,645 A | 1/1972 | Beam et al. |
| 3,687,076 A | 8/1972 | Friant et al. |
| 3,840,136 A | 10/1974 | Lanfranconi et al. |
| 3,917,063 A | 11/1975 | Chibret et al. |
| 4,024,952 A | 5/1977 | Leitz |
| 4,982,875 A | 1/1991 | Pozzi et al. |
| 5,058,770 A | 10/1991 | Herold et al. |
| 5,170,888 A | 12/1992 | Goncalves |
| 5,273,760 A | 12/1993 | Oshlack et al. |
| 5,419,445 A | 5/1995 | Kaesemeyer |
| 5,431,915 A | 7/1995 | Harvey et al. |
| 5,460,828 A | 10/1995 | Santus et al. |
| 5,472,712 A * | 12/1995 | Oshiack ............... A61K 9/2866 424/480 |
| 5,854,290 A | 12/1998 | Arnsten et al. |
| 5,955,106 A | 9/1999 | Moeckel et al. |
| 6,148,996 A | 11/2000 | Morini |
| 6,156,340 A | 12/2000 | Adeyeys et al. |
| 6,287,599 B1 | 9/2001 | Brunisde et al. |
| 6,676,966 B1 | 1/2004 | Odidi et al. |
| 6,811,794 B2 | 11/2004 | Burnside et al. |
| 6,890,957 B2 | 5/2005 | Chandran et al. |
| 7,214,387 B2 | 5/2007 | Sanghvi et al. |

(Continued)

FOREIGN PATENT DOCUMENTS

| | | |
|---|---|---|
| CN | 567978 A5 | 10/1975 |
| EP | 0601508 B1 | 3/1999 |

(Continued)

OTHER PUBLICATIONS

Ghulam Murtaza, Ethylcellulose Microparticles: A Review, 69 Drug Res. 11 (Year: 2012).*
Muschert, et al., Prediction of Drug Release from Ethylcellulose Coated Pellets, 135 J Control. Rel. 71 (Year: 2009).*
Intuiv: Highlights of prescribing information (201 X Shire US Inc, Revised Feb. 2013).
Kristine, "EKG Results/Tenex", Dr. Mom's Spot (Mar. 26, 2010) Available: http://drmomsspot.blogspot.com/2010/03/ekg-results-tenex.html.
Lopez-Liuchi et al., "Therapy for type 2 diabetes: where do we stand after the UK Prospective Diabetes Study?," European Journal of Endocrinology, 140:4-6 (1999).
Murtaza, "Ethylcellulose Microparticles: A Review," Drug Research, 69 (1):11-22 (2012).

(Continued)

*Primary Examiner* — Sean M Basquill
(74) *Attorney, Agent, or Firm* — Medler Ferro Woodhouse & Mills (57) ABSTRACT

The present invention relates to extended release liquid compositions of metformin. The extended release liquid compositions are in the form of suspensions or reconstituted powder for suspensions. Said extended release liquid compositions comprise cores of metformin coated with a release-controlling agent, wherein the coated cores are dispersed in a suspension base. Said extended release liquid compositions provide the desired uniform extended release profile throughout the shelf-life of the composition. Furthermore, said extended release liquid compositions are bioequivalent to a reference composition. It also relates to processes for the preparation of said extended release liquid compositions.

1 Claim, 3 Drawing Sheets

(56) References Cited

U.S. PATENT DOCUMENTS

| | | | |
|---|---|---|---|
| 7,748,550 B2 | 7/2010 | Cho | |
| 7,906,145 B2 * | 3/2011 | Castan | A61K 9/5042 |
| | | | 424/489 |
| 8,002,734 B2 | 8/2011 | Bassarab et al. | |
| 8,197,850 B2 | 6/2012 | Castan et al. | |
| 8,297,456 B1 | 10/2012 | Anderson | |
| 8,318,210 B2 | 11/2012 | Tengler et al. | |
| 8,453,833 B2 | 6/2013 | Porter | |
| 8,491,935 B2 | 7/2013 | Mehta et al. | |
| 8,541,018 B2 | 9/2013 | Radke et al. | |
| 8,960,424 B1 | 2/2015 | Anderson | |
| 9,132,950 B1 | 9/2015 | Anderson et al. | |
| 2001/0032643 A1 | 10/2001 | Hochrainer et al. | |
| 2003/0171407 A1 * | 9/2003 | Freese | A61K 31/366 |
| | | | 514/342 |
| 2003/0199846 A1 | 10/2003 | Fowles et al. | |
| 2004/0062800 A1 | 4/2004 | Burnside et al. | |
| 2004/0062802 A1 | 4/2004 | Hermelin | |
| 2004/0109891 A1 | 6/2004 | Sanghvi et al. | |
| 2005/0279653 A1 | 12/2005 | Williams-lucas et al. | |
| 2006/0193877 A1 | 8/2006 | Tengler et al. | |
| 2007/0193894 A1 | 8/2007 | Macken et al. | |
| 2008/0008765 A1 | 1/2008 | Schwarz et al. | |
| 2008/0095855 A1 | 4/2008 | Shwarz | |
| 2008/0118570 A1 | 5/2008 | Liu et al. | |
| 2008/0124432 A1 | 5/2008 | Ma | |
| 2008/0202950 A1 | 8/2008 | Anderson | |
| 2008/0314775 A1 | 12/2008 | Owoc | |
| 2009/0123538 A1 | 5/2009 | Alani et al. | |
| 2009/0142378 A1 | 6/2009 | Frisbee | |
| 2009/0176691 A1 | 7/2009 | Bennis et al. | |
| 2009/0325938 A1 | 12/2009 | Lichter et al. | |
| 2010/0092562 A1 | 4/2010 | Hollenbeck et al. | |
| 2010/0282624 A1 | 11/2010 | Paganuzzi | |
| 2010/0330150 A1 * | 12/2010 | Venkatesh | A61K 9/5084 |
| | | | 424/439 |
| 2011/0268808 A1 | 11/2011 | Jain et al. | |
| 2011/0313046 A1 | 12/2011 | Ermer | |
| 2012/0178666 A1 | 7/2012 | Franklin et al. | |
| 2012/0220930 A1 | 8/2012 | Griffiths et al. | |
| 2013/0109659 A1 | 5/2013 | Ranzani et al. | |
| 2014/0050796 A1 | 2/2014 | Tengler et al. | |
| 2014/0309271 A1 | 10/2014 | Price | |
| 2014/0319141 A1 | 10/2014 | Stratis et al. | |
| 2015/0021214 A1 | 1/2015 | Basic et al. | |
| 2016/0228360 A1 | 8/2016 | Kumar et al. | |
| 2016/0228379 A1 | 8/2016 | Kumar et al. | |
| 2016/0271070 A1 | 9/2016 | Singh et al. | |
| 2016/0317388 A1 | 11/2016 | Bhargava et al. | |
| 2016/0346233 A1 | 12/2016 | Singh et al. | |
| 2016/0346235 A1 | 12/2016 | Singh et al. | |
| 2017/0119627 A1 | 1/2017 | Gambino et al. | |
| 2017/0216142 A1 | 8/2017 | Mittal et al. | |
| 2017/0304234 A1 | 10/2017 | Singh et al. | |
| 2017/0312177 A1 | 11/2017 | Bhargava et al. | |
| 2018/0064663 A1 | 3/2018 | Singh et al. | |
| 2018/0133399 A1 | 5/2018 | Kumar et al. | |
| 2018/0221290 A1 | 8/2018 | Singh et al. | |
| 2018/0221314 A1 | 8/2018 | Singh et al. | |

FOREIGN PATENT DOCUMENTS

| | | |
|---|---|---|
| EP | 1122186 A1 | 8/2001 |
| EP | 1140027 B1 | 10/2005 |
| FR | 2897267 A1 | 8/2017 |
| JP | 2012514632 | 6/2012 |
| WO | WO2000/038655 A1 | 7/2000 |
| WO | WO2004/012715 A1 | 4/2004 |
| WO | WO2005/097040 A1 | 10/2005 |
| WO | WO2006/030297 A1 | 3/2006 |
| WO | WO2006/086856 A | 7/2008 |
| WO | WO2008/122993 A1 | 10/2008 |
| WO | WO2010/045656 A3 | 4/2010 |
| WO | WO2011/077451 A3 | 6/2011 |
| WO | WO2011/107855 A3 | 9/2011 |
| WO | WO2011/150506 A1 | 12/2011 |
| WO | WO2012/052853 A2 | 4/2012 |
| WO | WO2012/063257 A3 | 5/2012 |
| WO | WO2013/043064 A1 | 3/2013 |
| WO | WO2013/091882 A1 | 6/2013 |
| WO | WO2014/174119 A1 | 10/2014 |
| WO | WO2015/166472 A1 | 11/2015 |
| WO | WO2015/166473 A1 | 11/2015 |
| WO | WO2016/016845 A1 | 2/2016 |
| WO | WO2016/178130 A1 | 11/2016 |
| WO | WO2016/178131 A1 | 11/2016 |
| WO | WO2016/178132 A1 | 11/2016 |
| WO | WO2017/182851 A1 | 10/2017 |
| WO | WO2017/182852 A1 | 10/2017 |
| WO | WO20177182852 A1 | 10/2017 |
| WO | WO2017/191485 A1 | 11/2017 |

OTHER PUBLICATIONS

Steeman, 2009. Innovative dispensing bottle caps for sensitive vitamins [online]. Best In Packaging.

Medela Breast Milk Bottis Set, Target, published on or before 2010.

Timmins et al., "Steady-State Pharmacokinet of a Novel Extended-Release Metformin Formulation", Clinical Pharmacokinet., 44(7):721-729 (2005).

PCT/IB2015/053207 International Search Report and Written Opinion issued by US/ISA dated Aug. 7, 2015.

PCT/IB2015/053207 International Preliminary Reporton Patentability issued by WIPO dated Mar. 16, 2016.

PCT/IB2015/053209 International Search Report and Written Opinion issued by US/ISA dated Aug. 14, 2015.

PCT/IB2015/053209 International Preliminary Report on Patentability issued by WIPO dated Nov. 10, 2016.

PCT/IB2015/055780 International Search Report and Written Opinion issued by US/ISA dated Dec. 7, 2015.

PCT/IB2015/055780 International Preliminary Reporton Patentability issued by WIPO dated Feb. 9, 2017.

PCT/IB2016/052484 International Search Report and Written Opinion for International issued by US/ISA dated Sep. 8, 2016.

PCT/IB2016/052484 International Preliminary Report on Patentability issued by WIPO dated Nov. 16, 2017.

PCT/IB2016/052485 International Search Report and Written Opinion issued by US/ISA dated Aug. 31, 2016.

PCT/IB2016/052485 International Preliminary Reporton Patentability issued by WIPO dated Nov. 16, 2017.

PCT/IB2016/052486 International Search Report and Written Opinion issued by US/ISA dated Sep. 9, 2016.

PCT/IB2016/052486 International Preliminary Report on Patentability issued by WIPO dated Nov. 16, 2017.

PCT/IB2016/052488 International Search Report and Written Opinion issued by US/ISA dated Aug. 31, 2016.

U.S. Appl. No. 15/133,733 Restriction Requirement dated Jun. 10, 2016.

U.S. Appl. No. 15/133,773 Office Action dated Jul. 27, 2016.

U.S. Appl. No. 15/133,773 Final Office Action dated Dec. 16, 2016.

U.S. Appl. No. 15/133,773 Final Office Action dated Apr. 13, 2017.

U.S. Appl. No. 15/133,773 Office Action dated Aug. 1, 2017.

U.S. Appl. No. 15/133,773 Final Office Action dated Dec. 11, 2017.

U.S. Appl. No. 15/133,773 Office Action dated May 18, 2018.

U.S. Appl. No. 15/133,826 Restriction Requirement for dated Jun. 23, 2016.

U.S. Appl. No. 15/133,826 Restriction Requirement for dated Jul. 28, 2016.

U.S. Appl. No. 15/133,826 Final Office Action dated Dec. 20, 2016.

U.S. Appl. No. 15/133,826 Restriction Requirement for dated Feb. 14, 2017.

U.S. Appl. No. 15/133,826 Restriction Requirement for dated Feb. 12, 2018.

U.S. Appl. No. 15/144,000 Final Office Action dated Nov. 4, 2016.

U.S. Appl. No. 15/144,000 Office Action dated Feb. 14, 2017.

U.S. Appl. No. 15/144,000 Final Office Action dated Aug. 24, 2017.

U.S. Appl. No. 15/144,000 Final Office Action dated Mar. 14, 2018.

(56) References Cited

OTHER PUBLICATIONS

U.S. Appl. No. 15/144,026 Office Action dated Oct. 12, 2016.
U.S. Appl. No. 15/144,026 Final Office Action dated Apr. 6, 2017.
U.S. Appl. No. 15/144,026 Final Office Action dated Aug. 24, 2017.
U.S. Appl. No. 15/144,026 Final Office Action dated Feb. 7, 2018.
U.S. Appl. No. 15/144,058 Restriction Requirement dated Sep. 30, 2016.
U.S. Appl. No. 15/144,058 Office Action dated Dec. 16, 2016.
U.S. Appl. No. 15/144,058 Office Action dated May 11, 2017.
U.S. Appl. No. 15/144,058 Final Office Action dated Jul. 21, 2017.
U.S. Appl. No. 15/144,058 Office Action dated Jan. 16, 2018.
U.S. Appl. No. 15/144,098 Office Action dated Jul. 13, 2017.
U.S. Appl. No. 15/144,098 Final Office Action dated Feb. 22, 2018.
U.S. Appl. No. 15/148,069 Restriction Requirement dated Jul. 21, 2016.
U.S. Appl. No. 15/148,069 Office Action dated Nov. 2, 2016.
U.S. Appl. No. 15/148,069 Final Office Action dated Mar. 20, 2017.
U.S. Appl. No. 15/148,069 Office Action dated Aug. 10, 2017.
U.S. Appl. No. 15/148,069 Final Office Action dated Jan. 19, 2018.
U.S. Appl. No. 15/148,131 Office Action dated Oct. 7, 2016.
U.S. Appl. No. 15/148,131 Final Office Action dated Apr. 5, 2017.
U.S. Appl. No. 15/148,131 Office Action dated Sep. 29, 2017.
U.S. Appl. No. 15/148,131 Office Action dated Apr. 6, 2018.
U.S. Appl. No. 15/148,131 Final Office Action dated Aug. 6, 2018.
U.S. Appl. No. 15/329,070 Office Action dated Nov. 21, 2017.
U.S. Appl. No. 15/329,070 Final Office Action dated Jun. 11, 2018.
U.S. Appl. No. 15/942,840 Office Action dated May 29, 2018.
U.S. Appl. No. 15/352,993 Office Action dated Mar. 24, 2017.
U.S. Appl. No. 15/352,993 Office Action dated Aug. 24, 2017.
U.S. Appl. No. 15/352,993 Final Office Action dated Feb. 8, 2018.
U.S. Appl. No. 15/853,219 Final Office Action dated Sep. 6, 2018.
U.S. Appl. No. 15/800,682 Restriction Requirement dated Dec. 15, 2017.
U.S. Appl. No. 15/800,682 Office Action dated Apr. 10, 2018.
U.S. Appl. No. 15/942,711 Office Action dated Jun. 20, 2018.
U.S. Appl. No. 15/144,000 Office Action dated Aug. 31, 2018.
EP Application 15827750.9 Extended European Search Report dated Feb. 16, 2018.
EP Application 15786475.2 Extended European Search Report dated Nov. 13, 2017.
EP Application 16789381.7 Extended European Search Report dated Nov. 9, 2018.
EP Application 17210326.9 Extended European Search Report dated Jun. 3, 2018.
AU Application No. 2017254908 Office Action for dated Jun. 6, 2018.
AU Application No. 2017279809 Office Action dated Jun. 1, 2018.
Final Office Action issued in U.S. Appl. No. 15/800,682, dated Aug. 31, 2021.
Advisory Action issued in U.S. Appl. No. 15/800,682, dated Nov. 17, 2021.
Non-Final Office Action issued in U.S. Appl. No. 15/800,682, dated Jan. 25, 2022.

* cited by examiner

EXTENDED RELEASE LIQUID COMPOSITIONS OF METFORMIN

FIELD OF THE INVENTION

The present invention relates to stable extended release liquid compositions of metformin. The stable extended release liquid compositions are in the form of suspensions or reconstituted powder for suspensions. Said extended release liquid compositions comprise cores of metformin coated with a release-controlling agent, wherein the coated cores are dispersed in a suspension base. Said extended release liquid compositions provide the desired uniform extended release profile throughout the shelf-life of the compositions. Furthermore, said extended release liquid compositions are bioequivalent to a reference composition.

BACKGROUND OF THE INVENTION

Metformin, an effective anti-diabetic drug known for decades, acts by reducing glucose production by the liver and by decreasing intestinal absorption of glucose. Metformin improves glucose tolerance in patients with Type II diabetes and lowers both basal and post-prandial plasma glucose.

U.S. Pat. No. 8,197,850 discloses a medicament comprising microcapsules of a biguanide antihyperglycemic agent which comprises a core containing the biguanide antihyperglycemic agent and a prolonged release coating film which does not have a nitrogenous polymer, wherein the mean fraction by mass of the biguanide in the microcapsules is greater than 50%.

U.S. Pat. No. 7,214,387 discloses sustained-release pharmaceutical compositions of metformin comprising xanthan gum, locust bean gum, and a diluent, wherein therapeutically beneficial blood levels of metformin are maintained over a period of time from about 1 hour to about 24 hours.

U.S. Pat. No. 6,676,966 discloses an extended release formulation of metformin hydrochloride and an encasement coat in the form of one or more layers of pH-sensitive polymeric film, wherein said polymeric film is soluble in a pH of above 5.0.

Immediate release tablets of metformin marketed under the trade name of Glucophage® and an immediate release oral solution of metformin marketed under the trade name of Riomet® are administered multiple times a day, leading to a high level of non-compliance. Further, extended release tablets of metformin marketed under the trade name of Glucophage XR®, Fortamet®, and Glumetza® reduces the frequency of administration, but due to the large size of the tablets, the problem of patient compliance still remains. This problem is further aggravated in patients who have difficulty in swallowing, such as pediatric and geriatric patients. Furthermore, as metformin is indicated for chronic administration, such high levels of non-compliance may lead to non-adherence to the prescribed therapy, resulting in serious medical problems.

There exists a need in the art for extended release liquid compositions of metformin which provide effective control of blood glucose levels over a prolonged period of time, thereby leading to enhanced patient compliance and ease in administration. In view of this, extended release liquid compositions such as suspensions and reconstituted powder for suspensions provide the best alternative over the available dosage forms.

However, it remains a great challenge to formulate extended release liquid composition of metformin. The key hurdle remains to avoid the release of metformin from controlled release units into the suspension base during storage, and to begin release only when the dosage form enters the gastrointestinal tract. Because of its high solubility, metformin tends to leach out from the controlled release units into the suspension base during storage, thus obliterating the whole objective of the extended release. Furthermore, the irregular release may lead to sub-therapeutic or toxic effects leading to serious medical conditions.

The present invention addresses this problem by providing a simplified technology in which suspension base is used to prevent leaching of the metformin from the controlled release units into the suspension base. The present invention provides consistent in-vitro extended release of metformin which further ensures steady plasma concentrations throughout the shelf life of the composition. Furthermore, said extended release liquid compositions are bioequivalent to a reference composition.

Therefore, the present invention is a significant advance over the available dosage forms of metformin and also fulfills the long felt need to improve patient compliance by providing extended release liquid compositions of metformin.

Extended release liquid compositions of metformin of the present invention are simple, and easy to manufacture with functional reproducibility. The extended release liquid compositions are provided with a pleasant mouth feel thereby further aiding to patient compliance and ease of administration.

SUMMARY OF THE INVENTION

The present invention relates to stable extended release liquid compositions of metformin. The stable extended release liquid compositions are in the form of suspensions or reconstituted powder for suspensions. Said extended release liquid compositions comprise cores of metformin coated with a release-controlling agent, wherein the cores are dispersed in a suspension base. Said extended release liquid compositions provide the desired uniform extended release profile throughout the shelf-life of the composition. Furthermore, said extended release liquid compositions are bioequivalent to a reference composition. It also relates to processes for the preparation of said extended release liquid compositions.

The stable extended release liquid compositions of the present invention allow for dosing flexibility based on age and body weight of the patients. Said extended release liquid compositions provide high levels of patient compliance particularly for pediatric and geriatric group of patients. Also, as hypoglycemic therapy is frequently based on combinations of anti-diabetic drugs, the extended release liquid compositions of the present invention can incorporate any additional drug suitable for combination with metformin.

DETAILED DESCRIPTION OF THE INVENTION

A first aspect of the present invention provides a stable extended release liquid composition of metformin characterized by a $T_{max}$ in a range from about 3 hours to about 12 hours after a single dose administration under fed conditions.

According to one embodiment of the above aspect, the $T_{max}$ ranges from about 4 hours to about 10 hours. In a preferred embodiment of the above aspect, the $T_{max}$ ranges from about 5 hours to about 9 hours.

A second aspect of the present invention provides a stable extended release liquid composition of metformin providing therapeutic effectiveness for at least about 12 hours after a single dose administration under fed conditions. More particularly, the composition provides therapeutic effectiveness for at least about 24 hours after a single dose administration under fed conditions.

A third aspect of the present invention provides a stable extended release liquid composition of metformin characterized by a pharmacokinetic profile having one or more features of a $C_{max}$ from about 0.4 ng/mL/mg to about 2.5 ng/mL/mg; an area under the curve $(AUC)_{0\rightarrow\infty}$ from about 2.0 ng·h/mL/mg to about 22.0 ng·h/mL/mg; and an area under the curve $(AUC)_{0\rightarrow t}$ from about 2.5 ng·h/mL/mg to about 22.0 ng·h/mL/mg after a single dose administration under fed conditions.

A fourth aspect of the present invention provides a stable extended release liquid composition of metformin characterized in that the liquid composition is bioequivalent to a marketed extended release tablet of metformin.

According to one embodiment of the above aspect, the marketed extended release tablet of metformin is Glucophage XR® tablet, Fortamet® tablet, or Glumetza® tablet. Preferably, the marketed extended release tablet of metformin is Glucophage XR® tablet.

A fifth aspect of the present invention provides a stable extended release liquid composition of metformin comprising metformin hydrochloride in a concentration from about 25 mg/mL to about 500 mg/mL of the composition.

According to an embodiment of the above aspect, the composition comprises metformin hydrochloride in a concentration from about 50 mg/mL to about 200 mg/mL of the composition.

A sixth aspect of the present invention provides a method of lowering blood glucose levels in non-insulin dependent diabetes mellitus patients by administering a stable extended release liquid composition of metformin once daily or twice daily.

A seventh aspect of the present invention provides a stable extended release liquid composition of metformin characterized by having a substantially similar in-vitro dissolution release profile when tested in a dissolution media with a pH ranging from about 1 to about 7.

According to one embodiment of the above aspects, the composition comprises:
(i) cores of metformin coated with a release-controlling agent; and
(ii) a suspension base.

According to another embodiment of the above aspects, the composition is characterized by having an in-vitro dissolution release profile as determined by USP type II apparatus at 100 rpm, in 1000 mL of phosphate buffer with a pH 6.8 at 37° C. as follows:
less than 30% of metformin released after 0.5 hour;
less than 70% of metformin released after 2 hours; and
more than 85% of metformin released after 12 hours.

According to another embodiment of the above aspects, the in-vitro dissolution release profile of the composition remains substantially similar to the initial in-vitro dissolution release profile upon storage for at least seven days.

According to another embodiment of the above aspects, the composition is characterized by having an osmolality ratio of at least about 1.

According to another embodiment of the above aspects, the suspension base has an osmolality of about 1 osmol/kg or more than about 1 osmol/kg of the suspension base. In a particular embodiment, the suspension base has an osmolality of more than about 2 osmol/kg of the suspension base. In a more particular embodiment, the suspension base has an osmolality of more than about 3 osmol/kg of the suspension base.

According to another embodiment of above aspects, the suspension base is responsible for creating a hypertonic environment.

According to another embodiment of the above aspects, the suspension base comprises an osmogent.

According to another embodiment of the above aspects, the composition is a suspension or a reconstituted powder for suspension.

According to another embodiment of the above aspects, the release-controlling agent is selected from the group comprising a pH-dependent release-controlling agent, a pH-independent release-controlling agent, or mixtures thereof.

According to another embodiment of the above aspects, the core is in the form of a bead, a pellet, a granule, a spheroid, or the like.

According to another embodiment of the above aspects, metformin is layered onto an inert particle to form the core.

According to another embodiment of the above aspects, the composition has a pH ranging from about 4 to about 10.

According to another embodiment of the above aspects, the suspension base has a viscosity ranging from about 500 cps to about 15,000 cps. Preferably, the viscosity of the suspension base ranges from about 1,000 cps to about 10,000 cps. More preferably, the viscosity of the suspension base ranges from about 2,000 cps to about 7,000 cps. The viscosity of the suspension base of the present invention is measured by using a Brookfield Viscometer having a #2 spindle rotating at 5 rpm at 25° C.

According to another embodiment of the above aspects, the average diameter of the cores of metformin coated with a release-controlling agent ranges from about 10 µm to about 2000 µm, preferably from about 100 µm to about 1000 µm, and more preferably from about 150 µm to about 500 µm.

According to another embodiment of the above aspects, the suspension base does not comprise a saturated solution of metformin.

According to another embodiment of the above aspects, the composition is a taste masked composition.

An eight aspect of the present invention provides a process for the preparation of a stable extended release liquid composition of metformin, wherein the process comprises the steps of:
(i) preparing cores comprising metformin and one or more pharmaceutically acceptable excipients;
(ii) dissolving/dispersing a release-controlling agent and one or more pharmaceutically acceptable coating additives in a suitable solvent;
(iii) applying the coating composition of step (ii) over the cores of step (i);
(iv) dissolving/dispersing one or more osmogents and pharmaceutically acceptable excipients in a pharmaceutically acceptable vehicle to form a suspension base; and
(v) dispersing the coated cores of step (iii) in the suspension base of step (iv) to obtain the extended release liquid composition.

A ninth aspect of the present invention provides a process for the preparation of a stable extended release liquid composition of metformin, wherein the process comprises the steps of:
(A) preparing a powder for suspension comprising the steps of:
(i) preparing cores comprising metformin and one or more pharmaceutically acceptable excipients;
(ii) dissolving/dispersing a release-controlling agent and one or more pharmaceutically acceptable coating additives in a suitable solvent;
(iii) applying the coating composition of step (ii) over the cores of step (i);
(iv) blending the coated cores of step (iii) with pharmaceutically acceptable excipients to form the powder for suspension;
(B) dissolving/dispersing one or more osmogents and pharmaceutically acceptable excipients in a pharmaceutically acceptable vehicle to form a suspension base; and
(C) reconstituting the powder for suspension of step (A) with the suspension base of step (B) to obtain the extended release liquid composition.

A tenth aspect of the present invention provides a process for the preparation a stable extended release liquid composition of metformin, wherein the process comprises the steps of:
(A) preparing a powder for suspension comprising the steps of:
(i) preparing cores comprising metformin and one or more pharmaceutically acceptable excipients;
(ii) dissolving/dispersing a release-controlling agent and one or more pharmaceutically acceptable coating additives in a suitable solvent;
(iii) applying the coating composition of step (ii) over the cores of step (i);
(iv) mixing one or more osmogents and one or more pharmaceutically acceptable excipients with the coated cores of step (iii) to obtain the powder for suspension; and
(B) reconstituting the powder for suspension of step (A) with a pharmaceutically acceptable vehicle to obtain the extended release liquid composition.

According to another embodiment of the above aspects, the suspension base comprises an immediate release metformin component.

According to another embodiment of the above aspect, the extended release liquid composition further comprises one or more anti-diabetic drugs selected from the group comprising acarbose, miglitol, voglibose, repaglinide, nateglinide, glibenclamide, glimepride, glipizide, gliclazide, chloropropamide, tolbutamide, phenformin, aloglitin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, and combinations thereof.

The term "extended release," as used herein, refers to a release profile of metformin over an extended period of time, e.g., over a period of 4, 6, 8, 12, 24 hours, or more.

The in-vivo release profile can be assessed using pharmacokinetic parameters of ($C_{max}$), ($T_{max}$) and area under the curve (AUC).

The term "$C_{max}$," as used herein, refers to the maximum plasma concentration of metformin hydrochloride, calculated as the geometric mean for individuals participating in the bioequivalence study.

The term "$T_{max}$," as used herein, refers to the time to the maximum observed plasma metformin hydrochloride concentration, represented as a median for individuals participating in the bioequivalence study.

The term "$AUC_{0 \to \infty}$," as used herein, refers to the area under the plasma concentration-time curve extrapolated to infinity, calculated as the geometric mean for individuals participating in the bioequivalence study.

The term "$AUC_{0 \to t}$," as used herein, refers to the area under the plasma concentration-time curve till time t, calculated as the geometric mean for individuals participating in the bioavailability study.

The term "bioequivalent," as used herein, is a term of art and is defined to mean the term used by the drug approval agencies, such as the US Food and Drug Administration: "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." The ratios of the log transformed mean values for $C_{max}$ and AUC for the test and reference product (T/R ratio) is a measure of the bioequivalence between the test and reference product. Values between 80 and 125% for these intervals indicate bioequivalence as recommended by the US FDA.

The term "single dose," as used herein means the dose of metformin hydrochloride ranging from about 500 mg to about 2500 mg. In particular, the dose of metformin hydrochloride is 750 mg.

The stable extended release liquid composition of metformin provides a pharmacokinetic profile characterized by one or more features of a $C_{max}$ from about 0.4 ng/mL/mg to about 2.5 ng/mL/mg, more particularly a $C_{max}$ from about 0.5 ng/mL/mg to about 1.5 ng/mL/mg; an area under the curve $(AUC)_{0 \to \infty}$ from about 2.0 ng·h/mL/mg to about 22.0 ng·h/mL/mg, more particularly an area under the curve $(AUC)_{0 \to \infty}$, from about 5.0 ng·h/mL/mg to about 15.0 ng·h/mL/mg; an area under the curve $(AUC)_{0 \to t}$ from about 2.5 ng·h/mL/mg to about 22.0 ng·h/mL/mg, more particularly an area under the curve $(AUC)_{0 \to t}$ from about 5.0 ng·h/mL/mg to about 15.0 ng·h/mL/mg after a single dose administration under fed conditions.

Preferably, the stable extended release liquid composition of metformin comprising of the present invention provides a pharmacokinetic profile characterized by one or more features of: a $C_{max}$ from about 600 ng/mL to about 800 ng/mL, an area under the curve (AUC)$_{0\to\infty}$ from about 7500 ng·h/mL to about 9500 ng·h/mL, and an area under the curve (AUC)$_{0\to t}$ from about 7000 ng·h/mL to about 9000 ng·h/mL upon administration of a single dose equivalent to 750 mg of metformin hydrochloride under fed conditions.

The term "hypertonic environment," as used herein, means the suspension base has a higher solute concentration which helps to generate high osmotic pressure such that there is no leaching of metformin from the extended release coated cores into the suspension base. In the present invention, the solutes are osmogents, i.e., pharmaceutically acceptable inert water-soluble compounds that contribute towards generating hypertonic environment in the suspension base.

The term "osmolality ratio," as used herein, means the ratio of osmolality of the external phase to the osmolality of the internal phase. The external phase herein means the suspension base without multiple coated cores of metformin. The internal phase herein means the coated cores of metformin. The osmolality of the internal phase is represented as the osmolality of the solution which prevents significant leaching of metformin from the coated cores into the solution. The leaching of metformin from the coated cores is determined by the difference in the osmolalities across the coating layer and the absence of any significant leaching from the coated cores directs that the osmolality of the solution has become equal to the osmolality of the coated cores. The osmolality ratio of the extended release liquid compositions of present invention is at least about 1.

The term "osmolality," as used herein, means the concentration of an osmogent, i.e., any pharmaceutically acceptable inert water-soluble compound present in the suspension base. In the present invention, the osmolality is expressed as number of moles of any water-soluble compound per kg of a liquid phase. The liquid phase can be a suspension base or a solution. In the present invention, the osmolality may be measured according to known methods, such as using a Vapor pressure Osmometer, a Colloid Osmometer, or a Freezing Point Depression Osmometer such as Osmomat® 030-D or Osmomat® 3000, in particular by a Freezing Point Depression Osmometer.

The osmolality of suspension base of the extended release liquid compositions of the present invention remains equivalent upon storage for at least seven days. Particularly, the osmolality of the suspension base measured after one month remains equivalent to the osmolality of the suspension base measured as soon as practicable after preparation of the extended release liquid compositions. More particularly, the osmolality of the suspension base measured after three months remains equivalent to the osmolality of the suspension base measured as soon as practicable after preparation of the extended release liquid compositions. More particularly, the osmolality of the suspension base measured after six months remains substantially similar to the osmolality of the suspension base measured as soon as practicable after preparation of the extended release liquid compositions. The equivalent osmolality of the suspension base ensures that there is no leaching of the metformin from the coated cores into the suspension base.

The in-vitro dissolution release profile of the extended release liquid compositions of the present invention upon storage for at least seven days remains substantially similar to the initial in-vitro dissolution release profile obtained as soon as practicable after preparation of the extended release liquid compositions. Particularly, the in-vitro dissolution release profile of the extended release liquid compositions of the present invention upon storage at room temperature for at least one month remains substantially similar to the initial in-vitro dissolution release profile obtained as soon as practicable after preparation of the extended release liquid compositions. More particularly, the in-vitro dissolution release profile of the extended release liquid compositions of the present invention upon storage at room temperature for at least three months remains substantially similar to the initial in-vitro dissolution release profile obtained as soon as practicable after preparation of the extended release liquid compositions. More particularly, the in-vitro dissolution release profile of the extended release liquid compositions of the present invention upon storage for at least six months remains substantially similar to initial in-vitro dissolution release profile obtained as soon as practicable after preparation of the extended release liquid compositions. The composition of the present invention shows an in-vitro dissolution release profile as determined by USP type II apparatus at 100 rpm, in 1000 mL of phosphate buffer with a pH 6.8 at 37° C. as follows:

less than 30% of metformin released after 0.5 hour;
less than 70% of metformin released after 2 hours; and
more than 85% of metformin released after 12 hours.

The above in-vitro dissolution release profile is determined by using a composition comprising metformin hydrochloride in a dose range from about 500 mg to about 2500 mg. In particular, the composition comprises metformin hydrochloride in a dose of about 750 mg.

The extended release liquid composition of the present invention also provides the consistent in-vivo release which ensures steady and predictable metformin release with minimal inter and intra subject variation throughout the shelf life of the composition.

The term "substantial," as used herein refers to any value which lies within the range as defined by a variation of up to ±15 from the average value.

The term "stable," as used herein, refers to chemical stability, wherein not more than 5% w/w of total related substances are formed on storage at 40° C. and 75% relative humidity (R.H.) or at 25° C. and 60% R.H. for a period of at least three months to the extent necessary for the sale and use of the composition.

The extended release liquid composition of the present invention may be in the form of a suspension or a reconstituted powder for suspension.

The term "suspension base," as used herein, refers to a medium which is used to suspend the coated cores of the metformin. The suspension base comprises a pharmaceutically acceptable vehicle, one or more osmogents, and pharmaceutically acceptable excipients. The powder for suspension having coated cores of metformin of the present invention may be reconstituted with the suspension base having osmogents, pharmaceutically acceptable excipients, and a pharmaceutically acceptable vehicle. Alternatively, osmogents and pharmaceutically acceptable excipients may be mixed with the coated cores of metformin which may then be reconstituted with a pharmaceutically acceptable vehicle. In case of powder for suspension, the suspension base may be pre-formed or formed at the time of reconstitution. The suspension base of the present invention does not include a saturated solution of metformin.

The suspension base has an osmolality of about 1 osmol/kg or more than about 1 osmol/kg of the suspension base. The suspension base of the present invention has an osmolality ranging from about 1 osmol/kg to about 20 osmol/kg of the suspension base.

The pharmaceutically acceptable vehicle as used herein means an aqueous vehicle.

The term "inert particle," as used herein, refers to a particle made from a sugar sphere also known as a nonpareil seed, a microcrystalline cellulose sphere, a dibasic calcium phosphate bead, a mannitol bead, a silica bead, a tartaric acid pellet, a wax based pellet, and the like.

The term "about," as used herein, refers to any value which lies within the range defined by a variation of up to ±10% of the value.

The term "equivalent" as used herein, refers to any value which lies within the range defined by a variation of up to ±30% of the value.

The term "significant leaching," as used herein means more than 20% of the metformin is leached out from the coated cores into the solution.

The term "metformin," as used herein, refers to metformin as well as its pharmaceutically acceptable salts, polymorphs, hydrates, solvates, prodrugs, chelates, and complexes. The preferred salt of metformin is metformin hydrochloride. The extended release liquid compositions of the present invention comprise metformin in a range of from 1% to about 30% w/w based on total weight of the composition. In particular, the extended release liquid compositions of the present invention comprise metformin in a range of from 5% to about 20% w/w based on total weight of the composition.

The suspension base may additionally include an immediate release component of the metformin. However, the suspension base of the present invention does not include any saturated solution of the metformin. The suspension base may include an immediate release component of the metformin, wherein the metformin is present in an amount that does not exceed the amount required to form the saturated solution either initially or during storage. The metformin may be present in the form of a powder, a pellet, a bead, a spheroid, or a granule, or in the form of immediate release coating over the extended release coated cores. Alternatively, the amount of metformin may exceed the amount required to form the saturated solution. However, the saturated solution of metformin is not formed, as the release of metformin into the suspension base is prevented during storage. This is achieved by using a coating layer over cores of metformin, wherein the coating layer comprises a polymer that remain insoluble in the suspension base during storage and which releases the metformin in an immediate release form once ingested. Alternatively, this can also be done by using an ion-exchange resin complex approach, wherein the complex prevent any release of the metformin into the suspension base during storage, and release the metformin only when exposed to the physiological conditions upon ingestion. The polymer can be a water-soluble polymer in which the release of metformin is prevented by using a high molar concentration of the solutes in the suspension base, wherein the solutes have a higher affinity towards water in comparison to the polymer. Further, the polymer can be having a pH dependent solubility in which the release of metformin is prevented by using a pre-adjusted pH of the suspension base such that the polymer does not get dissolved in the suspension base but get dissolved when exposed to the physiological conditions. Metformin, being a cationic drug can be complexed with any of the known cation exchange resin like indion 244 and indion 264.

The immediate release component may help in providing an immediate therapeutic effect which could be subsequently followed by an extended therapeutic effect over a longer duration of time. In the present invention, the metformin may be present in the immediate release form in an amount of the about 0.5% to about 10% w/w based on total weight of the composition, particularly in an amount of about 1% to about 5% w/w based on total weight of the composition.

The extended release liquid compositions of the present invention may further include one or more anti-diabetic drugs such as acarbose, miglitol, voglibose, repaglinide, nateglinide, glibenclamide, glimepride, glipizide, gliclazide, chloropropamide, tolbutamide, phenformin, aloglitin, sitagliptin, linagliptin, saxagliptin, rosiglitazone, pioglitazone, troglitazone, faraglitazar, englitazone, darglitazone, isaglitazone, zorglitazone, liraglutide, muraglitazar, peliglitazar, tesaglitazar, canagliflozin, dapagliflozin, remogliflozin, sergliflozin, or any other known anti-diabetic drug The extended release liquid composition of the present invention are particularly suitable for anti-diabetic drugs which are incompatible with metformin. Additionally, extended release liquid composition of the present invention can incorporate anti-diabetic drugs having a low dose e.g., glibenclamide without altering the homogeneity of the composition. These anti-diabetic drugs may be present in the form of a powder, a pellet, a bead, a spheroid, or a granule providing immediate release or in the form controlled release coated cores providing the extended release.

The extended release liquid compositions of the present invention are homogeneous which means the compositions provide the content uniformity and deliver the desired dose of the metformin in every use without any risk of overdosing or underdosing.

The average diameter of the cores of metformin coated with a release-controlling agent ranges from about 10 μm to about 2000 μm, particularly from about 100 μm to about 1000 μm, and more particularly from about 150 μm to about 500 μm. Finer sizes of the coated cores help in avoiding grittiness in the mouth and thereby are easy and are more acceptable.

The cores of metformin coated with a release-controlling agent comprise metformin in an amount of about 10% to about 70% w/w based on the total weight of the coated cores, particularly from about 30% to about 50% w/w based on the total weight of the coated cores. The cores may comprise one or more pharmaceutically acceptable excipients such as binders.

The release-controlling agents used to form the extended release coating are selected from a group comprising a pH-dependent release-controlling agent, a pH-independent release-controlling agent, or mixtures thereof. For an extended release coating comprising a pH-dependent release-controlling agent, the pH of the suspension base is pre-adjusted such that the coating remains insoluble in the suspension base during the storage. The extended release coating comprising a pH-dependent release-controlling agent may alternatively be coated with a coating layer comprising a polymer such that said coating layer remain insoluble in the suspension base during storage. The core may comprise release-controlling agents in the form of a matrix with metformin, which can be coated with a coating layer that remain insoluble in the suspension base during storage.

Suitable examples of pH-dependent release-controlling agents are selected from the group comprising acrylic copolymers such as methacrylic acid and methyl methacrylate copolymers, e.g., Eudragit® L 100 and Eudragit® S 100, methacrylic acid and ethyl acrylate copolymers, e.g., Eudragit® L 100-55 and Eudragit® L 30 D-55, dimethylaminoethyl methacrylate and butyl methacrylate and methyl methacrylate copolymers e.g., Eudragit® E 100, Eudragit® E PO, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

Suitable examples of pH-independent release-controlling agents are selected from the group comprising cellulosic polymers such as ethyl cellulose, methyl cellulose, hydroxyethyl cellulose, hydroxypropyl cellulose, hydroxyethylmethyl cellulose, hydroxypropylmethyl cellulose, and carboxy methylcellulose; acrylic copolymers such as methacrylic acid copolymers, e.g., Eudragit® RS, Eudragit® RL, Eudragit® NE 30 D; cellulose acetate; polyethylene derivatives e.g., polyethylene glycol and polyethylene oxide; polyvinyl alcohol; polyvinyl acetate; gums e.g., guar gum, locust bean gum, tragacanth, carrageenan, alginic acid, gum acacia, gum arabic, gellan gum, and xanthan gum; triglycerides; waxes, e.g., Compritol®, Lubritab®, and Gelucires®; lipids; fatty acids or their salts/derivatives; a mixture of polyvinyl acetate and polyvinyl pyrrolidone, e.g., Kollidon® SR; and mixtures thereof. In particular, the pH-independent release-controlling agent used in the present invention is ethyl cellulose.

The term "osmogent," as used herein, refers to all pharmaceutically acceptable inert water-soluble compounds that can imbibe or dissolve in water and/or aqueous biological fluids. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide, xanthan gum, hydroxypropylmethyl cellulose; and mixtures thereof. Particularly, the osmogents used in the present invention are xylitol, mannitol, glucose, lactose, sucrose, and sodium chloride.

The term "pharmaceutically acceptable excipients," as used herein, refers to excipients that are routinely used in pharmaceutical compositions. The pharmaceutically acceptable excipients may comprise glidants, sweeteners, suspending agents, anti-caking agents, wetting agents, preservatives, buffering agents, flavoring agents, anti-oxidants, chelating agents, and combinations thereof.

Suitable glidants are selected from the group comprising silica, calcium silicate, magnesium silicate, colloidal silicon dioxide, cornstarch, talc, stearic acid, magnesium stearate, calcium stearate, sodium stearyl fumarate, hydrogenated vegetable, and mixtures thereof.

Suitable sweeteners are selected from the group comprising saccharine or its salts such as sodium, potassium, or calcium; cyclamate or its salt; aspartame; alitame; acesulfame or its salt; stevioside; glycyrrhizin or its derivatives; sucralose; and mixtures thereof.

Suitable suspending agents are selected from the group comprising cellulose derivatives such as co-processed spray dried forms of microcrystalline cellulose and carboxymethyl cellulose sodium, hydroxypropyl cellulose, hydroxyethyl cellulose, hydroxypropylmethyl cellulose, methylcellulose, carboxymethyl cellulose and its salts/derivatives, and microcrystalline cellulose; carbomers; gums such as locust bean gum, xanthan gum, tragacanth gum, arabinogalactan gum, agar gum, gellan gum, guar gum, apricot gum, karaya gum, sterculia gum, acacia gum, gum arabic, and carrageenan; pectin; dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; and mixtures thereof. The co-processed spray dried forms of microcrystalline cellulose and carboxymethyl cellulose sodium have been marketed under the trade names Avicel® RC-501, Avicel® RC-581, Avicel® RC-591, and Avicel® CL-611. The suspending agent is present in an amount of not more than about 20% w/w, based on the total weight of the suspension base.

Suitable anti-caking agents are selected from the group comprising colloidal silicon dioxide, tribasic calcium phosphate, powdered cellulose, magnesium trisilicate, starch, and mixtures thereof.

Suitable wetting agents are selected from the group comprising anionic, cationic, nonionic, or zwitterionic surfactants, or combinations thereof. Suitable examples of wetting agents are sodium lauryl sulphate; cetrimide; polyethylene glycols; polyoxyethylene-polyoxypropylene block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid ester such as polyoxyethylene sorbitan monooleate; polyethylene glycol fatty acid ester such as polyoxyethylene monostearate; polyoxyethylene alkyl ether such as polyoxyethylene lauryl ether; polyoxyethylene castor oil; and mixtures thereof.

Suitable preservatives are selected from the group comprising parabens such as methyl paraben and propyl paraben; sodium benzoate; and mixtures thereof.

Suitable buffering agents are selected from the group comprising citric acid, sodium citrate, sodium phosphate, potassium citrate, acetate buffer, and mixtures thereof.

Suitable flavoring agents are selected from the group comprising peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloe vera balsam, spearmint, eucalyptus, and combinations thereof.

Suitable anti-oxidants are selected from the group comprising butylated hydroxytoluene (BHT), butylated hydroxyanisole (BHA), sodium metabisulfite, ascorbic acid, propyl gallate, thiourea, tocopherols, beta-carotene, and mixtures thereof.

Suitable chelating agents are selected from the group comprising ethylenediamine tetraacetic acid or derivatives/salts thereof, e.g., disodium edetate; dihydroxyethyl glycine;

glucamine; acids, e.g., citric acid, tartaric acid, gluconic acid, and phosphoric acid; and mixtures thereof.

Suitable binders are selected from the group comprising polyvinyl pyrrolidone, starch, pregelatinized starch, hydroxypropylmethyl cellulose, hydroxyethyl cellulose, methyl cellulose, sodium carboxymethyl cellulose, gums, acrylate polymers, and mixtures thereof.

The cores of the present invention comprising metformin can be prepared by any method known in the art, e.g., extrusion-spheronoization, wet granulation, dry granulation, hot-melt extrusion granulation, spray drying, and spray congealing. Alternatively, metformin can be layered onto an inert particle to form the core.

Further, metformin can be directly coated with a release-controlling agent to form the microparticles or microcapsules. The microparticles or microcapsules can be prepared by a process of homogenization, solvent evaporation, coacervation phase separation, spray drying, spray congealing, polymer precipitation, or supercritical fluid extraction.

The extended release liquid compositions of the present invention may further comprise one or more seal coating layers which may be applied before and/or after the functional coating layer. The seal coating layer may comprise of one or more film forming polymers and coating additives.

Examples of film-forming polymers include ethylcellulose, hydroxypropyl methylcellulose, hydroxypropylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; methacrylic acid polymers such as Eudragito. Alternatively, commercially available coating compositions comprising film-forming polymers marketed under various trade names, such as Opadry® may also be used.

The coating additives used in the present invention are selected from the group comprising plasticizers, opacifiers, anti-tacking agents, coloring agents, and combinations thereof.

Suitable plasticizers are selected from the group comprising triethyl citrate, dibutylsebacate, triacetin, acetylated triacetin, tributyl citrate, glyceryl tributyrate, diacetylated monoglyceride, rapeseed oil, olive oil, sesame oil, acetyl tributyl citrate, acetyl triethyl citrate, glycerin, sorbitol, diethyl oxalate, diethyl phthalate, diethyl malate, diethyl fumarate, dibutyl succinate, diethyl malonate, dioctyl phthalate, and combinations thereof.

Suitable opacifiers are selected from the group comprising titanium dioxide, manganese dioxide, iron oxide, silicon dioxide, and combinations thereof.

Suitable anti-tacking agents are selected from the group comprising talc, magnesium stearate, calcium stearate, stearic acid, silica, glyceryl monostearate, and combinations thereof.

Suitable coloring agents are selected from the group consisting of FD&C (Federal Food, Drug and Cosmetic Act) approved coloring agents; natural coloring agents; natural juice concentrates; pigments such as iron oxide, titanium dioxide, and zinc oxide; and combinations thereof.

Coating may be performed by applying the coating composition as a solution/suspension/blend using any conventional coating technique known in the art, such as spray coating in a conventional coating pan, fluidized bed processor, dip coating, or compression coating. The percentage of the coating build-up shall be varied depending on the required extended release.

Suitable solvents used for granulation or for forming a solution or dispersion for coating are selected from the group comprising water, ethanol, methylene chloride, isopropyl alcohol, acetone, methanol, and combinations thereof.

The extended release liquid compositions of the present invention may be packaged in a suitable package such as a bottle. The powder for suspension may be packaged in a suitable package such as a bottle or a sachet. Further, the sachet can be filled as a unit dose or a multidose sachet. The present invention further includes a co-package or a kit comprising two components, wherein one package or one component comprises a powder for suspension and another package or another component comprises a suspension base or a pharmaceutically acceptable vehicle. Alternatively, a dual chamber pack with two chambers can be used. In this case, one chamber comprises a powder for suspension and another chamber comprises a suspension base or an aqueous vehicle.

The invention may be further illustrated by the following example, which is for illustrative purposes only and should not be construed as limiting the scope of the invention in any way.

EXAMPLES

Example 1

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 45.00 |
| Dibutyl sebacate | 1.50 |
| Acetone | q.s. |
| Purified water | q.s. |
| Total Weight of Extended Release Beads | 186.50 mg |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Strawberry flavor | 2.00 |
| Sucralose | 0.50 |
| Sodium benzoate | 3.00 |
| Colloidal silicon dioxide | 3.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose—sodium carboxymethyl cellulose, xanthan gum, strawberry flavor, sucralose, sodium benzoate, and colloidal silicon dioxide were mixed.

6. The coated beads of step 4 were mixed with the mixture of step 5 to obtain a powder for suspension.
7. The powder for suspension of step 6 is reconstituted with purified water when required to form the extended release liquid composition.

In-Vitro Studies

The extended release liquid composition prepared as per Example 1 was stored at room temperature for 66 days. The in-vitro dissolution was determined at 0, 30, and 66 days using USP type II apparatus at 100 rpm, in 1000 mL of phosphate buffer with pH 6.8 at 37° C. The results of the release studies are represented in Table 1.

TABLE 1

Percentage (%) of the In-Vitro Metformin Release in USP Type II Apparatus (Media: Phosphate Buffer, pH 6.8, 1000 mL, and 100 rpm)

| Number of Days | 0 | 30 | 66 |
|---|---|---|---|
| Time (hours) | Percentage of Metformin Release | | |
| 0.5 | 27.0 | 25.6 | 26.3 |
| 1 | 30.9 | 31.5 | 31.6 |
| 2 | 56.9 | 58.3 | 50.9 |
| 3 | 74.9 | 72.8 | 70.6 |
| 4 | 85.6 | 81.7 | 81.6 |
| 5 | 89.1 | 87.7 | 87.4 |
| 6 | 94.9 | 90.3 | 92.3 |
| 8 | 97.7 | 93.5 | — |
| 10 | 99.4 | 95.3 | — |
| 12 | 103.4 | 99.4 | 100.0 |

From the above data, it is clear that the extended release liquid composition prepared according to Example 1 provides substantially similar in-vitro metformin release for 66 days.

The powder for suspension prepared as per Example 1 (till step 6) was kept for one month at accelerated conditions i.e., 40° C./75% R.H. After one month, the powder for suspension was reconstituted with required amount of purified water and this extended release suspensions composition was kept for 66 days at room temperature. The in-vitro dissolution was determined at 0, 30, and 66 days using USP type II apparatus at 100 rpm, in 1000 mL of phosphate buffer with pH 6.8 at 37° C. The results of the release studies are represented in Table 2.

TABLE 2

Percentage (%) of the In-Vitro Metformin Release in USP Type II Apparatus (Media: Phosphate Buffer, pH 6.8, 1000 mL, and 100 rpm)

| Number of Days After Reconstitution | 0 | 36 | 66 |
|---|---|---|---|
| Time (hours) | Percentage of Metformin Release | | |
| 0.5 | 28.8 | 26.2 | 27.0 |
| 1 | 32.4 | 33.0 | 32.0 |
| 2 | 57.6 | 50.5 | 53.0 |
| 3 | 74.8 | 70.3 | 67.0 |
| 4 | 83.1 | 80.7 | 83.0 |
| 5 | 89.2 | 85.9 | 87.0 |
| 6 | 91.3 | 91.2 | 92.0 |
| 8 | 95.2 | — | 95.0 |
| 10 | 96.6 | — | 97.0 |
| 12 | 98.6 | 101.3 | 100.0 |

Figure 1:
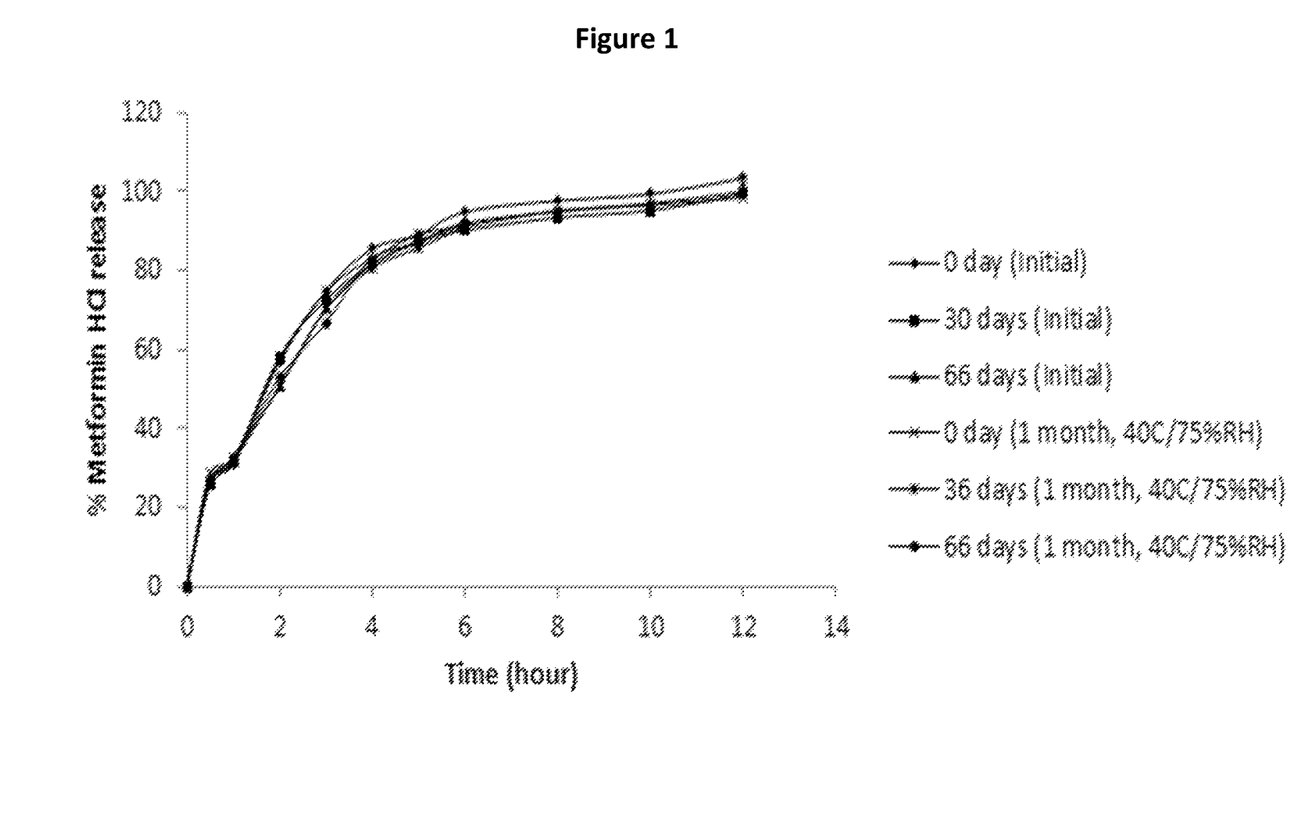
FIG. 1 shows the in-vitro dissolution release on day 0, day 30, and day 66 of the extended release liquid composition prepared according to Example 1 upon storage at room temperature. The figure also shows the in-vitro dissolution release on day 0, day 36, and day 66 of the extended release liquid composition (at room temperature) formed after reconstituting the powder stored for one month at accelerated conditions.

From the above data, it is clear that the extended release powder prepared according to Example 1 stored at accelerated conditions for one month, upon reconstitution and storage for 66 days at room temperature provides substantially similar in-vitro metformin release for 66 days. The results are shown in FIG. 1.

Example 2

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 50.40 |
| Dibutyl sebacate | 5.60 |
| Acetone | q.s. |
| Purified water | q.s. |
| Total Weight of Extended Release Beads | 196.00 mg |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Strawberry flavor | 2.00 |
| Sucralose | 0.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose—sodium carboxymethyl cellulose, xanthan gum, strawberry flavor, and sucralose were mixed.
6. The coated beads of step 4 were mixed with the mixture of step 5 to form a powder for suspension.
7. The powder for suspension of step 6 is reconstituted with purified water when required to form the extended release liquid composition.

In-Vitro Studies

The extended release liquid composition prepared as per Example 2 was stored at room temperature for 30 days. The in-vitro dissolution was determined at 0 and 30 days using a USP type II apparatus at 100 rpm, in 1000 mL of phosphate buffer with pH 6.8 at 37° C. The results of the release studies are represented in Table 3.

TABLE 3

Percentage (%) of the In-Vitro Metformin Release in USP Type II Apparatus (Media: Phosphate Buffer, pH 6.8, 1000 mL, and 100 rpm)

| Number of Days | 0 | 30 |
|---|---|---|
| Time (hours) | Percentage of Metformin Release | |
| 0.5 | 22 | 24 |
| 1 | 31 | 34 |

TABLE 3-continued

Percentage (%) of the In-Vitro Metformin Release in USP Type II Apparatus (Media: Phosphate Buffer, pH 6.8, 1000 mL, and 100 rpm)

| Number of Days Time (hours) | 0 | 30 |
|---|---|---|
| | Percentage of Metformin Release | |
| 2 | 58 | 61 |
| 4 | 83 | 89 |
| 5 | 86 | 93 |
| 6 | 91 | 96 |
| 8 | 95 | 101 |
| 10 | 97 | 102 |
| 12 | 99 | 103 |

From the above data, it is clear that the extended release liquid composition prepared according to Example 2 provides a substantially similar in-vitro metformin release profile for 30 days.

The powder for suspension prepared as per Example 2 (until step 6) was kept for three months at accelerated conditions 40° C./75% R.H. After three months, the powder for suspension was reconstituted with required amount of purified water and this extended release suspensions composition was kept for 30 days at room temperature. The in-vitro dissolution was determined at 0 and 32 days using USP type II apparatus at 100 rpm, in 1000 mL of phosphate buffer with pH 6.8 at 37° C. The results of the release studies are represented in Table 4.

TABLE 4

Percentage (%) of the In-Vitro Metformin Release in USP Type II Apparatus (Media: Phosphate Buffer, pH 6.8, 1000 mL, and 100 rpm)

| Number of Days After Reconstitution Time (hours) | 0 | 32 |
|---|---|---|
| | Percentage of Metformin Release | |
| 0.5 | 22 | 26 |
| 1 | 33 | 37 |
| 2 | 60 | 66 |
| 4 | 85 | 90 |
| 5 | 89 | 94 |
| 6 | 92 | 97 |
| 8 | 96 | 101 |
| 10 | 98 | 103 |
| 12 | 101 | 103 |

The powder for suspension prepared as per Example 2 (till step 6) was kept for six months at accelerated conditions i.e., 40° C./75% R.H. After six months, the powder for suspension was reconstituted with required amount of purified water and this extended release suspensions composition was kept for 32 days at room temperature. The in-vitro dissolution was determined at 0 and 32 days using USP type II apparatus at 100 rpm, in 1000 mL of phosphate buffer with pH 6.8 at 37° C. The results of the release studies are represented in Table 5.

TABLE 5

Percentage (%) of the In-Vitro Metformin Release in USP Type II Apparatus (Media: Phosphate Buffer, pH 6.8, 1000 mL, and 100 rpm)

| Number of Days After Reconstitution Time (hours) | 0 | 32 |
|---|---|---|
| | Percentage of Metformin Release | |
| 0.5 | 24 | 25 |
| 1 | 35 | 34 |
| 2 | 63 | 60 |
| 4 | 87 | 86 |
| 5 | 91 | 91 |
| 6 | 94 | 94 |
| 8 | 97 | 98 |
| 10 | 99 | 101 |
| 12 | 99 | 101 |

Figure 2:
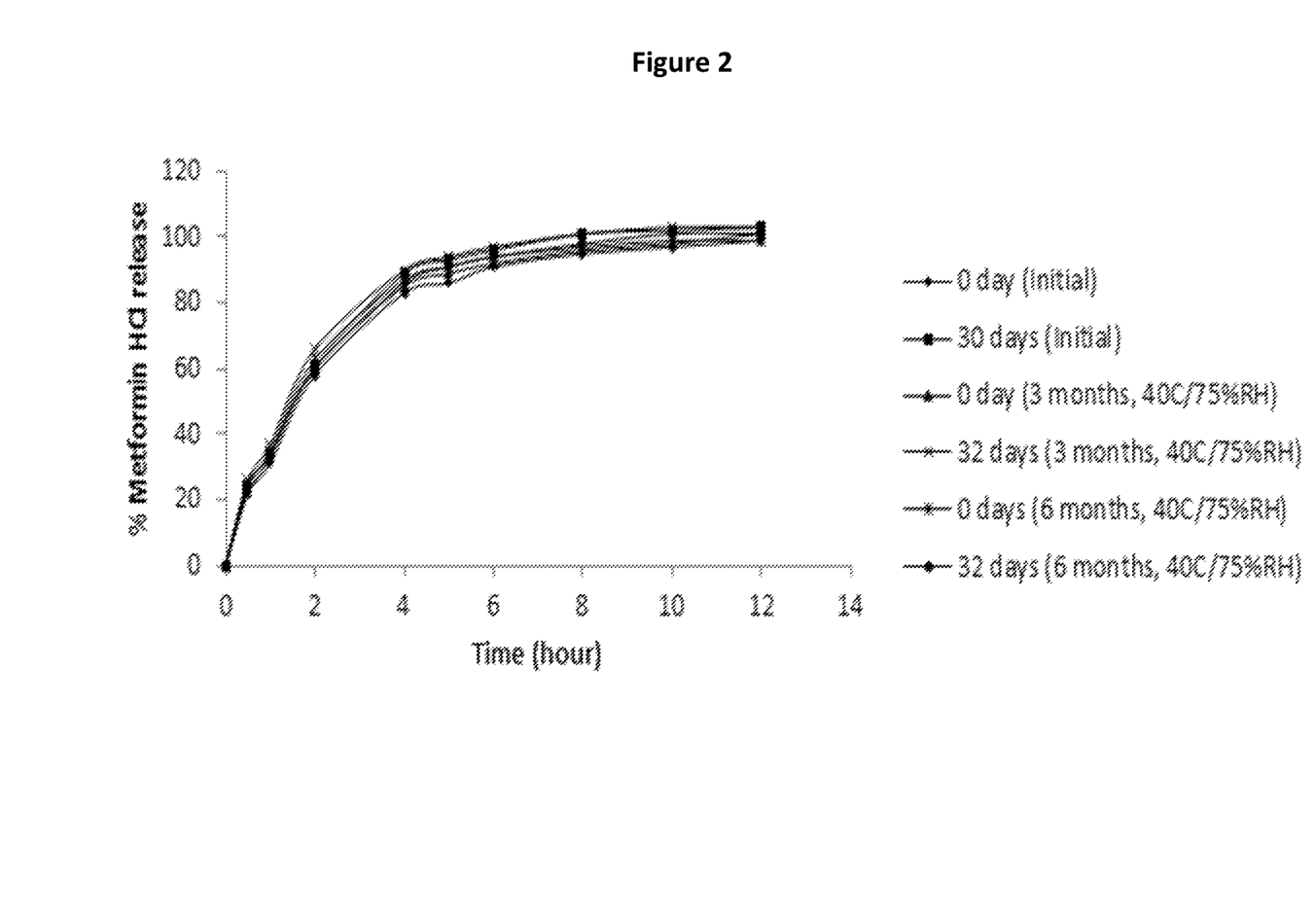
FIG. 2 shows the in-vitro dissolution release on day 0 and day 30 of the extended release liquid composition prepared according to Example 2 upon storage at room temperature. The figure also shows the in-vitro dissolution release on day 0 and day 32 of the extended release liquid composition (at room temperature) formed after reconstituting the powder stored for three months and six months at accelerated conditions.

From the above data, it is clear that the extended release powder prepared according to Example 2 and stored at accelerated conditions for three or six months, upon reconstitution and storage for 30 days at room temperature, provides a substantially similar in-vitro metformin release for 30 days. The results are presented in FIG. 2.

Example 3

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 61.48 |
| Dibutyl sebacate | 1.52 |
| Acetone | q.s. |
| Purified water | q.s. |
| Total Weight of Extended Release Beads | 203.00 mg |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Strawberry flavor | 2.00 |
| Sucralose | 0.50 |
| Colloidal silicon dioxide | 3.50 |
| Vehicle | |
| Purified water | q.s. to 1 mL |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3.
5. Metformin hydrochloride, xylitol, microcrystalline cellulose—sodium carboxymethyl cellulose, xanthan gum, strawberry flavor, sucralose, and colloidal silicon dioxide were mixed.
6. The coated beads of step 4 were mixed with the mixture of step 5 to form a powder for suspension.

7. The powder for suspension of step 6 is reconstituted with required amount of purified water when required to form the extended release liquid composition.

In-Vitro Studies

The extended release liquid composition prepared as per Example 3 was stored at room temperature for 30 days. The in-vitro dissolution was determined at 0 and 30 days using a USP type II apparatus at 100 rpm, in 1000 mL of phosphate buffer with pH 6.8 at 37° C. The results of the release studies are represented in Table 6.

TABLE 6

Percentage (%) of the In-Vitro Metformin Release in USP Type II Apparatus (Media: Phosphate Buffer, pH 6.8, 1000 mL, and 100 rpm)

| Number of Days Time (hours) | 0 | 30 |
|---|---|---|
| | Percentage of Metformin Release | |
| 0.5 | 20 | 22 |
| 1 | 27 | 28 |
| 2 | 59 | 64 |
| 3 | 77 | 80 |
| 4 | 84 | 89 |
| 5 | 88 | 93 |
| 6 | 92 | 95 |
| 8 | 95 | 99 |
| 10 | 97 | 101 |
| 12 | 98 | 103 |

From the above in-vitro release data, it is evident that the extended release liquid composition prepared according to Example 3 provides the substantially similar in-vitro release for 30 days.

The powder for suspension prepared as per Example 3 (till step 6) was kept for one month at accelerated conditions i.e., 40° C./75% R.H. After one month, the powder for suspension was reconstituted with purified water and kept for 30 days at room temperature. The in-vitro dissolution profile was determined at 0 and 30 days using a USP type II apparatus at 100 rpm, in 1000 mL of phosphate buffer with pH 6.8 at 37° C. The results of the release studies are represented in Table 7.

TABLE 7

Percentage (%) of the In-Vitro Metformin Release in USP Type II Apparatus (Media: Phosphate Buffer, pH 6.8, 1000 mL, and 100 rpm)

| Number of Days After Reconstitution Time (hours) | 0 | 30 |
|---|---|---|
| | Percentage of Metformin Release | |
| 0.5 | 20 | 19 |
| 1 | 26 | 26 |
| 2 | 57 | 57 |
| 3 | 74 | 74 |
| 4 | 82 | 80 |
| 5 | 86 | 85 |
| 6 | 90 | 88 |
| 8 | 92 | 91 |
| 10 | 94 | 93 |
| 12 | 96 | 94 |

Figure 3:
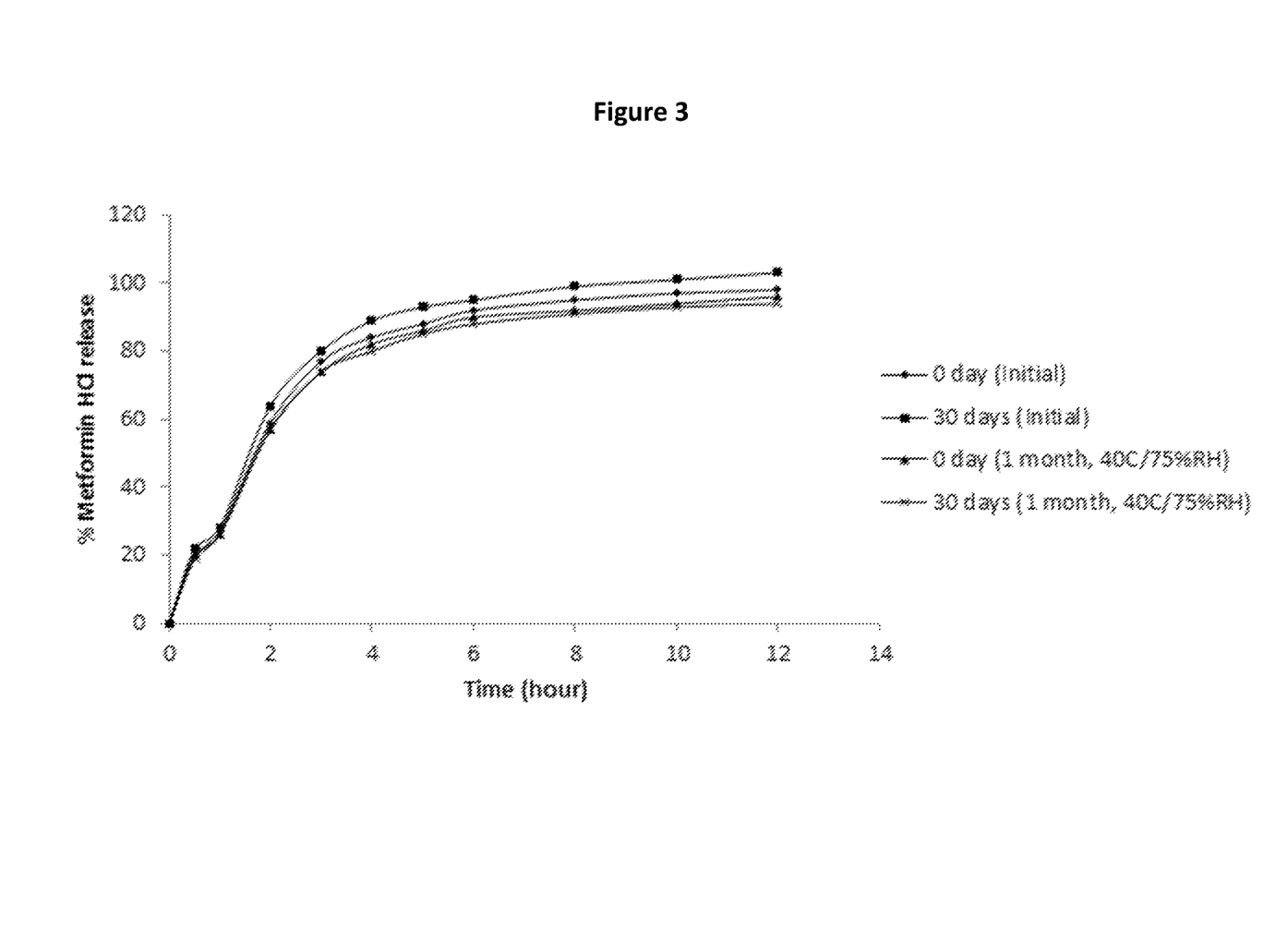
FIG. 3 shows the in-vitro dissolution release on day 0 and day 30 of the extended release liquid composition prepared according to Example 3 upon storage at room temperature. The figure also shows the in-vitro dissolution release on day 0 and day 30 of the extended release liquid composition (at room temperature) formed after reconstituting the powder stored for one month at accelerated conditions.

From the above data, it is clear that the extended release powder prepared according to Example 3 stored at accelerated condition for one month, upon reconstitution and storage for 30 days at room temperature provides substantially similar in-vitro metformin release for 30 days. The results are presented in FIG. 3.

Osmolality Measurement of the Extended Release Suspension

The metformin extended release powder prepared according to the Example 3 (till step 6) was reconstituted with purified water. This suspension was shaken manually for at least 20 minutes. This suspension was then filtered and diluted with purified water and the osmolality was measured using Osmomat® 030-D.

The osmolality of the suspension base was found to be 4.112 osmol/kg of the suspension base on day 0.

The osmolality of the suspension base was found to be 4.328 osmol/kg of the suspension base on day 7.

It is evident from the above data that the osmolality of the suspension base of the extended release liquid composition as per Example 3 remains equivalent for seven days.

Osmolality Measurement of the External Phase

The metformin hydrochloride, xylitol, microcrystalline cellulose—sodium carboxymethyl cellulose, xanthan gum, strawberry flavor, sucralose, and colloidal silicon dioxide were mixed as per step 6 of Example 3. This powder was reconstituted with purified water. This suspension was then filtered and diluted with purified water and the osmolality was measured using Osmomat® 030-D.

The osmolality of the suspension base i.e., external phase was found to be 4.204 osmol/kg of the suspension base.

Osmolality Measurement of the Internal Phase

Various solutions having various concentrations of osmogent (sodium chloride) were prepared as per Examples 3A-3F. The osmolalities of these solutions were measured using Osmomat® 030-D.

| Ingredient | Example 3A | Example 3B | Example 3C | Example 3D | Example 3E | Example 3F |
|---|---|---|---|---|---|---|
| Sodium Chloride (mg) | 30.00 | 60.00 | 120.00 | 180.00 | 240.00 | 300.00 |
| Purified water | q.s. to 1 mL | q.s. to 1 mL | q.s. to 1 mL | q.s. to 7.5 mL | q.s. to 1 mL | q.s. to 1 mL |
| Osmolality (osmol/kg) | 0.910 | 1.787 | 3.574* | 5.361* | 7.148* | 8.935* |

*Extrapolated using values of dilute solutions

The coated beads of step 4 of Example 3 were dispersed in different solutions as per Examples 3A-3F. These solutions were kept for seven days at room temperature. After seven days, each solution was analyzed by HPLC for metformin content. The results are represented in Table 8.

TABLE 8

Effect of Osmolality on Metformin Leaching

| Example | Osmolality (osmol/kg) of the solution | Metformin Content (%) |
|---|---|---|
| 3A | 0.910 | 67.3 |
| 3B | 1.787 | 30.3 |
| 3C | 3.574* | 2.9 |
| 3D | 5.361* | 1.8 |
| 3E | 7.148* | 1.7 |
| 3F | 8.935* | 1.0 |

*Extrapolated using values of dilute solutions

From the above data, it is evident that the leaching of metformin from the coated beads into the solution was decreasing as the osmolality of the solution was increasing from Examples 3A-3F. The leaching is found to be significantly reduced from Example 3C onwards. The osmolality of the formulation prepared according to Example 3C is considered to be the osmolality of the internal phase.
Osmolality Ratio 1.176
Dose Uniformity Data The extended release suspension equivalent to 100 mL was prepared according to formula given in Example 3. This suspension was shaken manually for at least 20 minutes and then ten 7.5 mL samples were taken with a graduated syringe. The metformin content of each sample is determined by HPLC method [Inertsil ODS column (250×4.6 mm, 5 μm); mobile phase-buffer (pH 3.5):acetonitrile (95:5 v/v); flow rate of 1.5 mL/min; UV detection at 233 nm] The results are shown in Table 9.

TABLE 9

Metformin Content (%) For Each 7.5 mL of Suspension

| Sample Number | Metformin content for 7.5 mL of suspension (%) |
|---|---|
| 1 | 98.6 |
| 2 | 97.9 |
| 3 | 96.6 |
| 4 | 97.2 |
| 5 | 99.7 |
| 6 | 96.4 |
| 7 | 95.9 |
| 8 | 97.3 |
| 9 | 98.8 |
| 10 | 96.9 |
| Mean value | 97.5 |

Form the above data, it is evident that the extended release liquid composition prepared according to Example 3 is homogeneous.
Assay Data The assay for the extended release liquid composition prepared as per Example 3 was determined at 0 day and after storage at room temperature for 30 days. The powder for suspension prepared as per Example 3 (till step 7) was kept for one month at accelerated conditions i.e., 40° C./75% R.H. After one month, the powder for suspension was reconstituted with purified water and then the assay was determined at day 0 and after storage at room temperature for 30 days. The assay of metformin was determined by HPLC [Inertsil ODS column (250×4.6 mm, 5 μm); mobile phase-buffer (pH 3.5):acetonitrile (95:5 v/v); flow rate of 1.5 mL/min; UV detection at 233 nm]. The results are shown in Table 10.

TABLE 10

Assay for Metformin

| | % Assay (After reconstitution) | |
|---|---|---|
| Condition | 0 day | 30 days |
| Initial | 97.0 | 99.5 |
| 1 month (40° C./75% R.H.) | 97.4 | 98.9 |

It is evident from the above data that the extended release liquid composition prepared as per Example 3 is stable.

The in-vitro dissolution of the formulation prepared according to Example 3 (7.5 mL of extended release suspension equivalent to 750 mg of metformin hydrochloride) was compared with commercially available Glucophage® XR Tablets 750 mg. The in-vitro dissolution was determined by using a USP type II apparatus at 100 rpm, in 1000 mL of phosphate buffer with pH 6.8 at 37° C. The results of the release studies are represented in Table 11.

TABLE 11

Comparative Dissolution Release Data of Example 3 and Glucophage ® XR Tablets

| Time (hours) | Percentage of Metformin Release from Example 3 | Percentage of Metformin Release from Glucophage ® XR Tablets |
|---|---|---|
| 0.5 | 18 | 21 |
| 1 | 22 | 33 |
| 2 | 45 | 49 |
| 3 | 66 | 61 |
| 4 | 76 | 70 |
| 5 | 83 | 77 |
| 6 | 86 | 83 |
| 8 | 90 | 90 |
| 10 | 92 | 94 |
| 12 | 94 | 96 |

Example 4

| Ingredients | Quantity (mg/mL) |
|---|---|
| Core | |
| Metformin hydrochloride | 80.00 |
| Microcrystalline cellulose spheres | 56.00 |
| Hydroxypropylmethyl cellulose | 4.00 |
| Purified water | q.s. |
| Extended Release Coating | |
| Ethyl cellulose | 68.31 |
| Dibutyl sebacate | 1.69 |
| Acetone | q.s. |
| Purified water | q.s. |
| Total Weight of Extended Release Beads | 210.00 mg |
| Suspension Base | |
| Metformin hydrochloride | 20.00 |
| Xylitol | 450.00 |
| Microcrystalline cellulose - sodium carboxymethyl cellulose (Avicel ® CL-611) | 20.00 |
| Xanthan gum | 1.50 |
| Methyl paraben | 1.80 |

| Ingredients | Quantity (mg/mL) |
|---|---|
| Propyl paraben | 0.20 |
| Strawberry flavor | 2.00 |
| Sucralose | 0.50 |
| Colloidal silicon dioxide | 3.50 |
| Purified water | 472.00 mg |

Procedure:
1. Metformin hydrochloride and hydroxypropylmethyl cellulose were dissolved in purified water.
2. Microcrystalline cellulose spheres were coated with the solution of step 1.
3. Ethyl cellulose and dibutyl sebacate were dispersed in a mixture of acetone and purified water.
4. The beads of step 2 were coated with the coating dispersion of step 3 and dried to form a powder for suspension.
5. Purified water was heated to dissolve methyl paraben and propyl paraben.
6. Metformin hydrochloride, xylitol, microcrystalline cellulose—sodium carboxymethyl cellulose, xanthan gum, strawberry flavor, sucralose, and colloidal silicon dioxide were mixed in the solution of step 5 to form a suspension base.
7. The powder for suspension of step 4 was prefilled in the second chamber of a dual-chamber pack.
8. The suspension base of step 7 was prefilled in a container of a first chamber of a dual-chamber pack.
9. The two chambers were assembled and the pack was activated to form the extended release liquid composition when required.

In-Vitro Studies

The extended release liquid composition prepared as per Example 4 (for a dose equivalent to 750 mg of metformin hydrochloride) was stored at room temperature for 120 days. The in-vitro dissolution was determined at 0, 45, 90, and 120 days using USP type II apparatus at 100 rpm, in 1000 mL of phosphate buffer with pH 6.8 at 37° C. The results of the release studies are represented in Table 12.

TABLE 12

Percentage (%) of the In-Vitro Metformin Release in USP Type II Apparatus (Media: Phosphate Buffer, pH 6.8, 1000 mL, and 100 rpm)

| Number of Days | 0 | 45 | 90 | 120 |
|---|---|---|---|---|
| Time (hours) | Percentage of Metformin Release | | | |
| 0.5 | 20 | 21 | 20 | 21 |
| 1 | 27 | 25 | 27 | 25 |
| 2 | 55 | 52 | 55 | 52 |
| 3 | 74 | 72 | 74 | 72 |
| 4 | 83 | 81 | 83 | 81 |
| 5 | 85 | 86 | 85 | 86 |
| 6 | 87 | 90 | 87 | 90 |
| 8 | 91 | 94 | 91 | 94 |
| 10 | 93 | 96 | 93 | 96 |
| 12 | 94 | 97 | 94 | 97 |

From the above in-vitro release data, it is evident that the extended release liquid composition prepared according to Example 4 provides the substantially similar in-vitro metformin release for 120 days.

The dual-chamber pack was kept for 1 month at accelerated conditions i.e., 40° C./75% R.H. After 1 month, the pack was activated to form an extended release liquid composition which was kept for 120 days at room temperature. The in-vitro dissolution was determined at 0, 45, 90, and 120 days using USP type II apparatus at 100 rpm, in 1000 mL of phosphate buffer with pH 6.8 at 37° C. The results of the release studies are represented in Table 13.

TABLE 13

Percentage (%) of the In-Vitro Metformin Release in USP Type II Apparatus (Media: Phosphate Buffer, pH 6.8, 1000 mL, and 100 rpm)

| Number of Days | 0 | 45 | 90 | 120 |
|---|---|---|---|---|
| Time (hours) | Percentage of Metformin Release | | | |
| 0.5 | 21 | 21 | 21 | 20 |
| 1 | 27 | 25 | 26 | 26 |
| 2 | 56 | 55 | 52 | 54 |
| 3 | 74 | 74 | 76 | 72 |
| 4 | 83 | 81 | 82 | 81 |
| 10 | 96 | 96 | 97 | 94 |

The dual-chamber pack was kept for 3 months at accelerated conditions i.e., 40° C./75% R.H. After 3 months, the pack was activated to form an extended release liquid composition which was kept for 45 days at room temperature. The in-vitro dissolution was determined at 0 and 45 days using USP type II apparatus at 100 rpm, in 1000 mL of phosphate buffer with pH 6.8 at 37° C. The results of the release studies are represented in Table 14.

TABLE 14

Percentage (%) of the In-Vitro Metformin Release in USP Type II Apparatus (Media: Phosphate Buffer, pH 6.8, 1000 mL, and 100 rpm)

| Number of Days | 0 | 45 |
|---|---|---|
| Time (hours) | Percentage of Metformin Release | |
| 0.5 | 21 | 21 |
| 1 | 26 | 25 |
| 2 | 55 | 53 |
| 3 | 75 | 72 |
| 4 | 80 | 80 |
| 10 | 95 | 92 |

From the above data, it is clear that the powder for suspension and suspension base stored in the dual-chamber pack of the instant invention at accelerated conditions for 1 month and 3 months, upon activation of the pack forms extended release liquid compositions which when stored for 120 days and 45 days respectively at room temperature provides substantially similar in-vitro metformin release.

Stability Data

The related substances for the extended release liquid composition prepared as per Example 4 were determined at 0 day and after storage at room temperature for 45 and 120 days. The powder for suspension and suspension base was stored in the dual-chamber pack for one month and for three months at 40° C./75% R.H. After one month or three months, the pack was activated to form an extended release liquid composition and then related substances were determined at 0 day and after storage at room temperature for 45 days and 120 days.

The assay of metformin was determined by HPLC method. The results are shown in Table 15.

TABLE 15

Stability Data for Metformin

| Related Substances (% w/w) | Initial | | | 1 month (40° C./75% R.H) | | | 3 month (40° C./75% R.H) | |
|---|---|---|---|---|---|---|---|---|
| | 0 day | 45 days | 120 days | 0 day | 45 days | 120 days | 0 day | 45 days |
| Cyanoguainidine | BLQ | 0.001 | 0.00072 | 0.001 | 0.001 | 0.001 | 0.001 | 0.001 |
| Highest unknown impurity | 0.05 | 0.05 | 0.04 | 0.05 | 0.04 | 0.04 | 0.05 | 0.04 |
| Total impurities | 0.05 | 0.05 | 0.04 | 0.05 | 0.04 | 0.04 | 0.09 | 0.04 |

*BLQ: Below limit of Quantification

It is evident from the above data that the extended release liquid composition prepared as per Example 4 remains stable even after storing at accelerated conditions for 3 months.

Osmolality of the Suspension Base:

3.960 osmol/kg of the suspension base as measured by using Osmomat® 030-D.

Viscosity of the Suspension Base:

2880 cps as measured by using Brookfield Viscometer using a #2 spindle rotating at 5 rpm at 25° C.

Example 5: Pharmacokinetic Study of Metformin Hydrochloride Extended Release Powder for Oral Suspension The extended release liquid composition of Example 3 having a concentration of about 100 mg/mL was dosed at an amount equivalent to 750 mg metformin hydrochloride and the single-dose pharmacokinetics was determined. This suspension was compared with a commercially available extended release composition of metformin hydrochloride (Glucophage® XR Tablet, 750 mg of Bristol Myers Squibb Company) in healthy adult human subjects underfed conditions.

Fourteen healthy adult subjects were enrolled in this open-label, two-treatment, two-period, two-sequence, single dose, crossover bioavailability study and randomly assigned to receive the 750 mg metformin hydrochloride extended release suspension of the present invention (Example 3) or the reference Glucophage® XR Tablet. Blood samples were collected at appropriate time intervals over a period of 48 hours and plasma concentrations of metformin were determined and pharmacokinetic parameters were calculated. Out of fourteen, thirteen subjects completed the study.

Pharmacokinetic Analysis

Values for metformin pharmacokinetic parameters, including observed $C_{max}$, $T_{max}$, $AUC_{0 \to t}$, and $AUC_{0 \to \infty}$, were calculated using standard noncompartmental method. The pharmacokinetic results obtained after single-dosing in the above study are summarized in Table 16.

TABLE 16

Comparative Pharmacokinetic Data

| Pharmacokinetic Parameters | Geometric mean of Test (T) Metformin Hydrochloride for Extended Release Liquid Composition 100 mg/mL (750 mg) (n = 13) | Geometric mean of Reference (R) Glucophage ® XR Metformin Hydrochloride Extended-Release Tablets 750 mg (n = 13) | Log Transformed T/R ratio of Least Square Means (%) | 90% Confidence Interval | Intra-subject CV % |
|---|---|---|---|---|---|
| $AUC_{0 \to t}$ (ng · h/mL) | 7786.18 | 8840.66 | 87.53 | 80.74-94.89 | 11.47 |
| $AUC_{0 \to \infty}$ (ng · h/mL) | 8051.95 | 9125.13 | 87.69 | 80.72-95.26 | 11.76 |
| $C_{max}$ (ng/mL) | 752.83 | 752.97 | 99.99 | 92.07-108.59 | 11.72 |
| $T_{max}$ * (h) | 6.5 | 7.5 | — | — | — |

$C_{max}$: Maximum observed plasma drug concentration $AUC_{0 \to t}$: Area under concentration-time curve from zero to time t $AUC_{0 \to \infty}$: Area under concentration-time curve from zero to infinity $T_{max}$: Time to maximum observed plasma drug concentration, represented as a median From the above table, it is clear that the 90% confidence intervals for the ratios of the log transformed mean values $C_{max}$ and $AUC_{0\to\infty}$, for the test and reference product (T/R ratio) were within the bioequivalence acceptance criteria.

Also, it is clear from the above data, the composition of the present invention shows a $C_{max}$ of 1.00 ng/mL/mg, $AUC_{0\to t}$ of 10.38 ng·h/mL/mg, and $AUC_{0\to\infty}$ of 10.74 ng·h/mL/mg after a single dose administration under fed conditions.

We claim:

1. A method of treating type II diabetes comprising orally administering once or twice a day to a patient in need thereof a stable extended release suspension composition, the composition comprising:
   a first component comprising an extended release powder form that comprises a coated core having an average diameter of about 150 μm to about 500 μm, wherein the coated core comprises metformin in the form of a bead, a pellet, a granule or a spheroid, and a releasing controlling agent comprising a polymer, wherein the releasing controlling agent is about 24% to about 50% (wt/wt) of the coated core; and
   a second component comprising a suspension base that comprises metformin in an immediate release form, one or more osmogents, one or more suspending agents, and pharmaceutically acceptable excipients, wherein the suspension base has an osmolality ranging from about 3 osmol/kg to about 20 osmol/kg, and wherein the suspension base does not comprise a saturated solution of metformin;
   wherein the first component and the second component are mixed together prior to administering to said patient,
   wherein, after mixing the first component and the second component, said polymer on the coating layer on the coated cores remains insoluble prior to administering to the patient,
   wherein, after mixing the first component and the second component, said stable extended release suspension composition comprises metformin at a concentration of about 100 mg/mL and releases less than 30% of metformin after 0.5 hour, less than 70% of metformin after 2 hours, and more than 85% of metformin after 12 hours when the in-vitro dissolution release profile is determined by USP type II apparatus at 100 rpm, in 1000 mL of phosphate buffer with a pH 6.8 at 37° C., and wherein the in-vitro dissolution profile of the suspension composition remains substantially similar to its initial in-vitro dissolution release profile upon storage for at least seven days.

* * * * *